US005360389A

United States Patent [19]
Chenette

[11] Patent Number: 5,360,389
[45] Date of Patent: Nov. 1, 1994

[54] METHODS FOR ENDOMETRIAL IMPLANTATION OF EMBRYOS

[76] Inventor: Philip E. Chenette, 290 Alhambra St. Apt. 3, San Francisco, Calif. 94123

[21] Appl. No.: 67,447
[22] Filed: May 25, 1993
[51] Int. Cl.⁵ ............................................. A61B 17/43
[52] U.S. Cl. ...................................................... 600/34
[58] Field of Search ...................................... 600/33–35

[56] References Cited

U.S. PATENT DOCUMENTS

| | | |
|---|---|---|
| 4,326,505 | 4/1982 | Cropsey . |
| 4,493,700 | 1/1985 | Cassou . |
| 4,642,094 | 2/1987 | North . |
| 4,654,025 | 3/1987 | Cassou et al. ........................ 600/35 |
| 4,701,161 | 10/1987 | Lenck ................................... 600/34 |
| 4,790,814 | 12/1988 | Fischl . |
| 4,832,681 | 5/1989 | Lenck . |
| 4,846,785 | 7/1989 | Cassou . |
| 4,863,423 | 9/1989 | Wallace . |
| 4,865,589 | 9/1989 | Simmet . |
| 5,084,004 | 1/1992 | Ranoux . |
| 5,147,315 | 9/1992 | Weber . |

OTHER PUBLICATIONS

David R. Meldrum et al., "Evolution of a highly successful in vitro fertilization–embryo transfer program" in:Fertility and Sterility, vol. 48, No. 1, Jul. 1987, pp. 86–93.
Alfred N. Poindexter, et al; "Residual embryos in failed embryo tranfer" in: Fertility and Sterility, vol. 46 No. 2 Aug. 1986, pp. 262–267.
John Leeton, et al, "The technique for human embryo transfer" in:Fertility and Sterility, vol. 38, No. 2 Aug. 1982, pp. 156–161.
Jacques Testart, "Evidence of uterine inadequacy to egg implantation in stimulated in vitro fertilization cycles" in Fertility and Sterility, vol. 47, No. 5, May 1987, pp. 855–857.
Giovanni Possati, et al., "Gamete intrafallopian transfer by hysteroscopy as an alternative treatment for infertility", vol. 56, No. 3, Sep. 1991, pp. 496–499.
Richard J. Paulson, "Embryo implantation after human in vitro fertilization: improtance of endometrial receptivity", in Fertility and Sterility, vol. 53, No. 5, May 1990, pp. 870–874.
Victor A. Hurley, "Ultrasound-guided embryo transfer: a controlled trial", in: Fertility and Sterility, vol. 55, No. 3, Mar. 1991, pp. 559–562.
Richard J. Paulson, "Factors affecting embryo implantation after human in vitro fertilization: A hypothesis", in: American Journal of Obstetrical Gynecology, Dec. 1990, pp. 2020–2023.
Carlo Bulletti, "Early human pregnancy in vitro utilizing an artificially perfused uterus", in: Fertility and Sterility, vol. 49, No. 6, Jun. 1988, pp. 991–996.
Yasuo Goto, et al, "Pregnancy achieved by transferring blastocysts into endometrial stroma in mice", in: Human Reproduction, vol. 7, No. 5, 1992, pp. 681–684.
Susan Lenz, "Intrauterine Fertilization Capsules-A Clinical Trial" in: Journal of in Vitro Fertilization and Embryo Transfer, vol. 8, No. 5, 1991, pp. 272–275.
Estela Maris A. F. Bevilacqua, "Growth of Mouse Embryos Implanted in the Subcutaneous Tissue of Recipient Mice", in: The Journal of Experimental Zoology 257:386–400 (1991).
Walter J. Cohen, et al, *Micromanipulation of Human Gametes and Embryos*, Raven Press, NY 1992, pp. 142–145.
O. Kato, et al, "Transmyometrial Embryo Transfer-The Towako Method-Experience of 104 Cases"-](Abstract) in PFCS Apr. 1992, A17.
S. I. Roh, "Transvaginal Ultrasonogrphy Directed Transmural Embryo Transfer", (Abstract) in AFS, Oct. 1991, p. S41.
Keel, et al, *CRC Hanbook of the Laboratory Diagnosis and Treatment of Infertility*, pp. 312–317.

Primary Examiner—Lee S. Cohen
Assistant Examiner—John P. Lacyk
Attorney, Agent, or Firm—Townsend and Townsend Khourie and Crew

[57] ABSTRACT

The invention provides methods for implantation of an embryo into a mammal comprising placing the embryo in a catheter, admitting the catheter through the mammal's cervical os into the endometrial cavity, directing a distal tip of the catheter into the mammal's uterine tissue, and depositing the embryo into the uterine tissue beneath the surface of or within the endometrial lining. Flushing the catheter with a physiologic solution assists in deposition of the embryo. Fiberoptic guidance can facilitate direction of the catheter tip and deposition of the embryo.

23 Claims, 3 Drawing Sheets

METHODS FOR ENDOMETRIAL IMPLANTATION OF EMBRYOS

BACKGROUND OF THE INVENTION

A trend toward minimally invasive therapy is apparent throughout the field of obstetrics and gynecology, with pressure from third party payers to reduce costs and a desire to speed therapy and minimize adverse effects on work productivity. Improvement in the pregnancy rate following in vitro fertilization can be a significant step toward this goal.

In vitro fertilization (IVF) involves the production of embryos outside the uterus with subsequent placement of the embryos into the uterus or fallopian tubes. Traditional techniques include ultrasound-guided transvaginal retrieval of eggs or oocytes followed by insemination with sperm obtained by masturbation. Transfer of embryos into the uterine or endometrial cavity typically occurs after culturing the embryos in vitro for 48 hours.

Traditional embryo transfer involves placement of up to eight embryos in 10 to 30 microliters of medium into a polytetrafluoroethylene or "TEFLON TM " catheter. The catheter passes through the cervical opening into the endometrial cavity. Subsequently the medium containing the embryos is discharged into the endometrial cavity. The procedure is performed blindly without visualizing the catheter tip or endometrium. The patient typically rests in the prone position for two hours following the transfer.

Several problems can arise with conventional embryo transfer. First, the embryos are relatively mobile following transfer. They are sometimes found attached to the catheter or in the cervix or vagina. They can also travel into the fallopian tube, as demonstrated by a higher rate of tubal gestation following in vitro fertilization as compared to normal conception.

Contractions and peristalsis of the uterine musculature produce movement of intrauterine fluids as demonstrated both radiographically and ultrasonically. Motion of embryos in this fluid can interfere with implantation. In addition, transcervical transfer disrupts the cervical mucous plug which normally prevents loss of embryos. Thus numerous mechanisms may contribute to embryo loss following conventional embryo transfer.

Another factor preventing pregnancies after enmbryo transfer is poor endometrial receptivity, both from hormonal over-stimulation of the endometrium and intrinsic anatomic defects. Use of hormones such as gonadotropins to stimulate follicular development causes poorly receptive endometrium by elevating estradiol levels and over-stimulating endometrial development. Electron microscopy has revealed excessive development of the ciliary border of the endometrium and clinical experience shows an increase in endometrial secretions with gonadotropin stimulation. Several classes of patients have distinct anatomic abnormalities affecting implantation capacity. Examples include myomas encroaching on the uterine cavity, uterine septa, endometrial polyps, and diethylstilbestrol (DES) exposure with its attendant defects, adhesions, vascular anomalies and endometritis. Age is also associated with decreased endometrial receptivity. If endometrial receptivity is inadequate, normal embryos are less likely to implant and produce pregnancy.

A mathematical model has been developed for pregnancy rates as a result of in vitro fertilization. The equation is:

$$PR = EQ \times ER \times TE \times N,$$

where
PR = Pregnancy rate,
EQ = Embryo quality,
ER = Endometrial receptivity,
TE = Embryo transfer efficiency, and
N = Number of embryos transferred.
See Paulson, et al. "Factors affecting embryo implantation after human in vitro fertilization: A hypothesis," *Am. J. Obstet. Gynecol.*, 163(6) 1:2020 (1990). By analysis and comparison of natural cycles, where endometrial receptivity should be ideal, with oocyte donor cycles, where embryo quality should be ideal, embryo transfer efficiency has been estimated at approximately 60%. A typical IVF cycle with embryo quality of 25%, endometrial receptivity of 50%, and transfer of four embryos, gives a pregnancy rate of roughly 30% per embryo transfer ($0.25 \times 0.50 \times 0.6 \times 4 = 0.3$). This is typical of a good IVF program. However, if transfer efficiency improved to 90%, pregnancy rates would rise by 50%, yielding a pregnancy rate of 45% per embryo transfer ($0.25 \times 0.5 \times 0.9 \times 4 = 0.45$).

Improving the results of in vitro fertilization depends in part on improving embryo transfer efficiency. A variety of transfer techniques are available, but they provide no more than 60% transfer efficiency. Current catheter and fiberoptic technology allows the development of better catheters and mechanisms for directly visualizing the endometrium. These technologies may enable treatment and superior management of the earliest stage of pregnancy, the time of implantation.

Hysteroscopy, or fiberoptic endoscopy of the uterus and/or fallopian tubes, has been used for transfer of gametes, sperm and/or ova to the fallopian tube for in vivo fertilization. Thus, hysteroscopy can be performed for the purpose of transferring gametes without significantly disrupting the endometrium or injuring the gametes. Catheters and hysteroscopes used in conjunction with the invention are composed of biologically inert materials used in Class III medical devices. A Class III medical device is allowed temporary direct blood conrace, generally for less than 24 hours.

SUMMARY OF THE INVENTION

A central focus of the invention is deposition of an embryo within the uterine lining or endometrium of a mammal. Preferably, the recipient mammal is a human. Visualization of the endometrium and visual guidance of deposition of the embryo are preferably practiced with the invention and can be provided by fiberoptic technology.

Conveniently, a method of the invention includes placing at least one embryo in a microcatheter having an elongate tubular body and a distal tip. Preferably, four to eight embryos are transferred per fertilization attempt. The distal tip of the catheter is introduced into the mammal's cervical os or opening and directed into the mammal's uterine tissue.

Preferably, the microcatheter has a non-stick surface to prevent the embryos from adhering to the catheter, thus assisting with embryo deposition. A non-stick surface can be formed of polytetrafluoroethylene which is commercially available under the trade name "TE- FLON ™". The microcatheter preferably measures about 0.1–1.0 millimeter (mm) in diameter and can deliver one or two embryos per fertilization attempt.

Methods of the invention are preferably performed with fiberoptic guidance to assist with steps such as introducing the microcatheter tip through the cervical opening and into the endometrial cavity, directing the tip into the uterine tissue, and depositing the embryo within the endometrial lining. The depth at which the embryo is deposited is typically from about 0.5 mm to about 5 mm beneath the endometrial surface. More preferably, the embryo is deposited at a depth of about 0.5 mm to about 2 mm. Most preferably, the embryo is deposited at a depth of about 1.0 mm.

The deposition of the embryo into the uterine tissue can be accomplished by flushing the microcatheter with a physiologic irrigant. Such irrigants are well known to the artisan and include amniotic or follicular fluid, saline solution, Ringer's solution and culture medium such as stock Ham's F-10 or Earle's medium (both available from GIBCO, New York).

A convenient method of practicing the invention involves the steps of selecting a microcatheter having an elongate tubular body and a distal tip having a non-stick surface, placing at least one embryo in the distal tip, introducing the distal tip through the cervical opening and into the endometrial cavity, directing the distal tip into the uterine tissue at a depth of about 0.5 mm to about 2 mm, and flushing the microcatheter with a physiologic irrigant thereby depositing the embryo into the uterine tissue at a depth of about 0.5 mm to about 2 mm.

Fiberoptic guidance can be used to assist with introduction of the distal tip of the microcatheter through the cervical opening into the endometrial cavity, directing the tip of the microcatheter into the uterine tissue, and flushing the microcatheter to deposit the embryo within the endometrial lining. Typically, fiberoptic guidance is provided by an endoscope of the type having an open channel. The channel is adapted for receipt of the microcatheter and is dimensioned to permit protrusion of the distal tip of the microcatheter from the distal end of the channel.

One or more microcatheters can be placed into a sleeve which is in turn placed into the channel of the endoscope. The sleeve preferably includes multiple, independently movable, translucent microcatheters which individually measure about 0.1–1.0 mm in diameter. Preferably, there are about two, three, or four microcatheters to each sleeve. The diameter of the sleeve is preferably from about 0.5 mm to about 2 mm. The distal tip of the sleeve can have a curved dimension to facilitate negotiating the curvature of the uterine cavity.

DESCRIPTION OF A PREFERRED EMBODIMENT

Figure 1A:
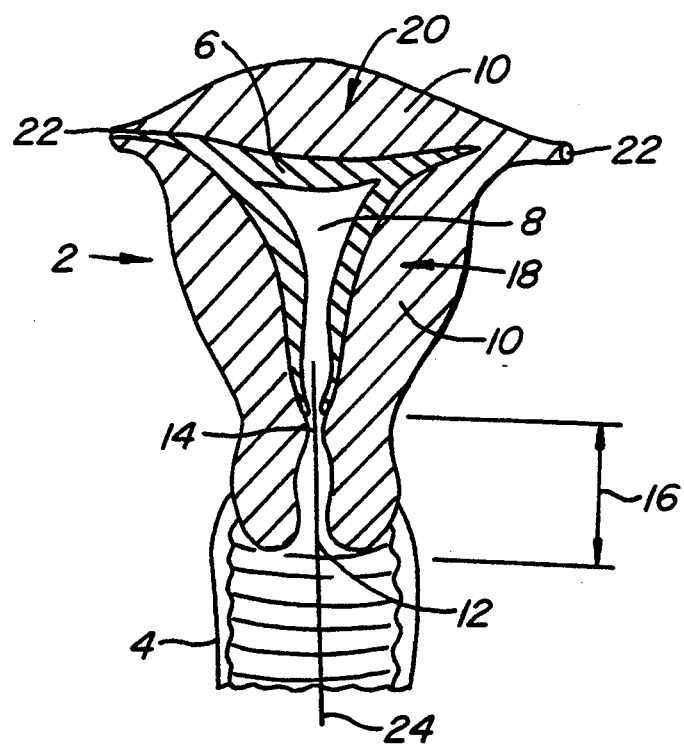
FIG. 1A is a schematic of a sagittal section of the human uterus and associated structures.
Figure 1B:
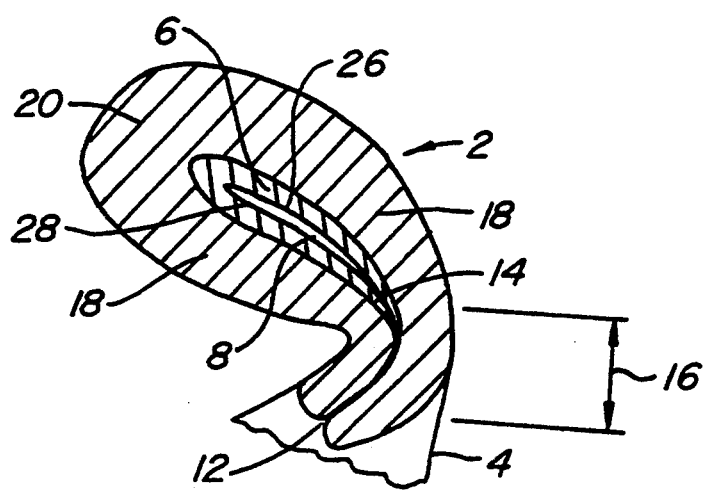
FIG. 1B is an anterior-posterior section of the human uterus.

The invention provides deposition of at least one embryo beneath the endometrial surface, preferably within the endometrium. See FIGS. 1A and 1B generally for anatomic references. The female reproductive system includes the vagina 4, the uterus 2, the fallopian tubes 22 and the ovaries (not shown). The cervix 16 includes the external cervical os 12 and the internal cervical os 14. The uterus is divided anatomically into the fundus 20 and the body 18. The uterus 2, both fundus 20 and body 18, is composed mainly of a muscular stroma called the myometrium 10. The myometrium is lined with the endometrium which is also called the uterine lining or endometrial lining 6. The endometrial cavity 8 or lumen is in communication with the cervix 16 and vagina 4. Line 24 indicates a path that a catheter may take to enter the uterine or endometrial cavity 8. FIG. 1B shows the posterior wall 26 and anterior wall 28 of the uterine cavity 8.

Figure 2A:
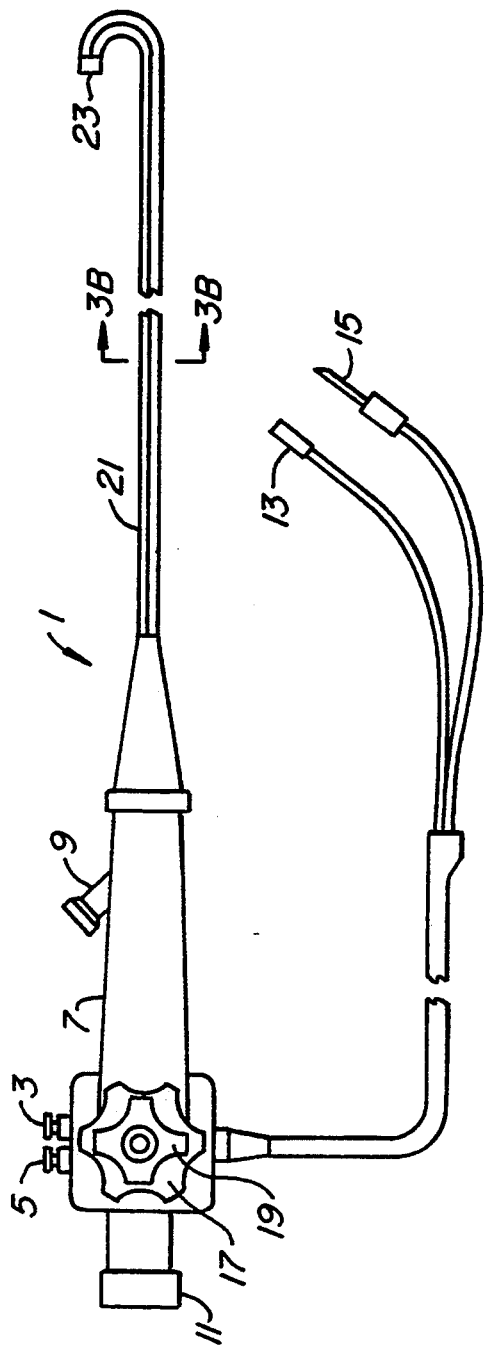
FIG. 2A is a schematic of a prior art fiberoptic endoscope.
Figure 2B:
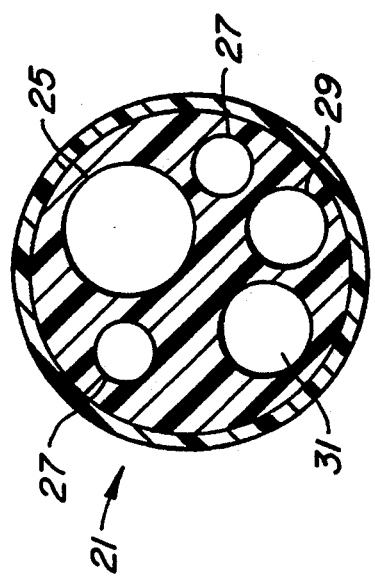
FIG. 2B shows a cross-sectional view of the endoscope.

A schematic of a conventional flexible fiberoptic endoscope or hysteroscope 1 is shown in FIG. 2A and a cross-sectional view is shown in FIG. 2B. Hysteroscope 1 typically includes a depressible button 3 to control gas and liquid influx, a control 5 to manipulate suction, and a control head 7. A biopsy channel inlet 9 is usually located on control head 7, as is an eye piece or viewing aperture 11. Hysteroscope 1 communicates with an external gas and/or suction device through end 13 and to an external light source through end 15. Knob 17 controls up and down deflection of a flexible tip 23 at the distal end of hysteroscope tube 21. Knob 19 controls left/right deflection of tip 23. A cross-sectional view of tube 21 includes a lens 25, a light source 27, an air and water channel 29, and a biopsy and suction channel 31.

In use, the operator inserts distal tip 23 into the vagina 4 of a patient, through the cervix 16 and into the patient's endometrial cavity 8. The operator can manipulate control knobs 17 and 19 to view an area of interest. Liquid and gases, such as water and air or carbon dioxide ($CO_2$), can be injected into the patient's endometrial cavity to assist in viewing an area clearly. Fluids can be removed by using the suction.

Figure 3A:
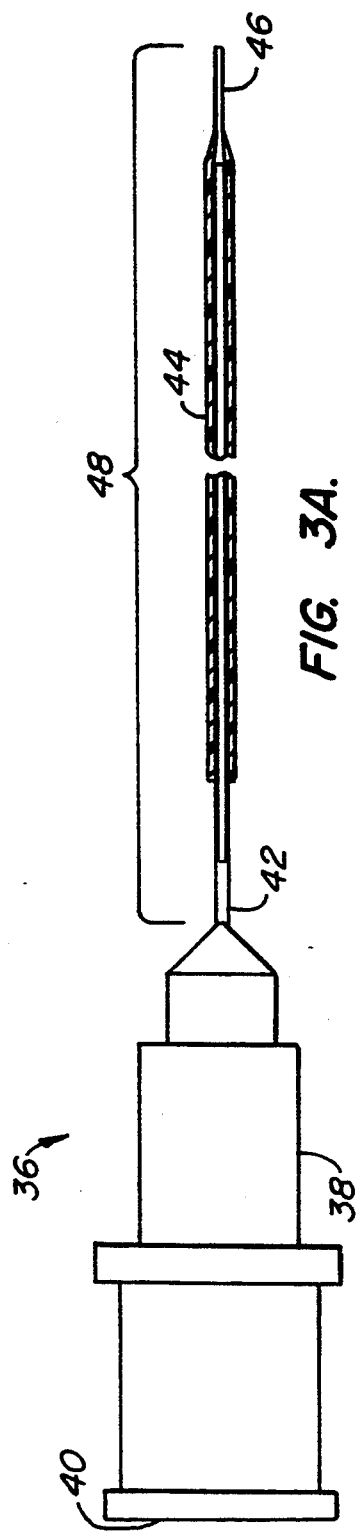
FIG. 3A is a schematic of a preferred microcatheter for use with the present invention.

A microcatheter of the invention is shown schematically in FIG. 3A. Microcatheter 36 includes a hub 38 of the type adapted to receive a syringe at opening 40. Typically, hub 38 includes an external Luer lock adapted to mate with a syringe. In fluid communication with opening 40 is an elongate tubular body 48. Body 48 includes a hollow flexible guide 42 which is preferably composed of a metallic substance, such as stainless steel. Body 48 also includes hollow guide shell 44 which houses a substantial portion of flexible guide 42, including the distal end of guide 42 and preferably includes an extension beyond the distal end of guide 42. Shell 44 is preferably composed of a plastic, such as a polyimide. Shell 44 terminates in a very flexible hollow tip having a diameter narrower than either shell 44 or guide 42. Hollow tip 46 preferably includes a very slick material, at least on its inner surface, such as "TEFLON" ™. Preferably, distal tip 46 includes external markings (not shown) at 3 mm, 5 mm and 10 mm from its distal end.

Figure 3B:
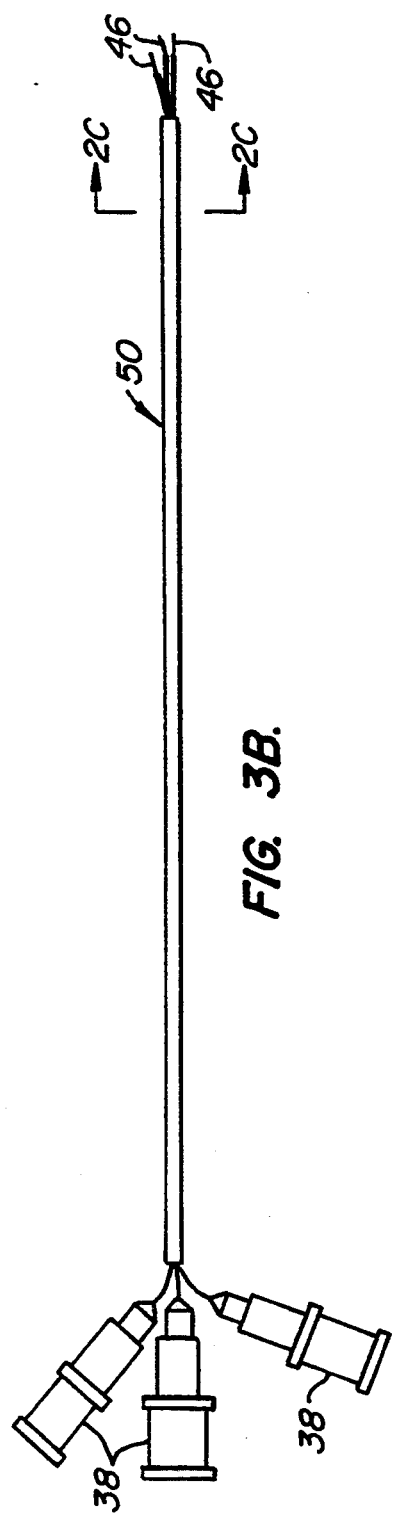
FIG. 3B shows a sleeve adapted to fit over at least one microcatheter.
Figure 3C:
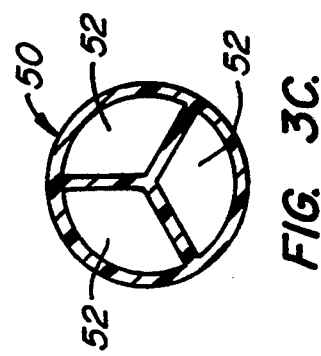
FIG. 3C shows a cross-sectional view of the sleeve.

A method of the invention can enable the near atraumatic deposition of at least one embryo within the uterine endometrium 6 under hysteroscopic (i.e. fiberoptic) visualization. The microcatheters are contained within a sleeve 50. Sleeve 50 preferably contains multiple independently movable translucent microcatheters 36 which individually measure about 0.1–1 mm in diameter (i.e. 1/10th the diameter of a conventional blind transfer catheter). Most preferably hollow sleeve 50 includes three inner ports dimensioned to accommodate one microcatheter 36 each. See FIGS. 3B and 3C. For general reference purposes, open end 40 of microcatheter 36 is at the end referred to as the proximal end and hollow tip 46 is at the end referred to as the distal end of microcatheter 36. Sleeve 50, containing microcatheter(s) 36, is positioned in an open channel of hysteroscope 1, preferably channel 31.

Each microcatheter can deliver at least one fertilized embryo per passage into the uterus. The distal end of each microcatheter is preferably sufficiently translucent to permit direct visualization of the embryo transfer process via hysteroscopic inspection and sufficiently sharp to enable a controlled penetration of the uterine endometrium with minimal difficulty. Endometrial penetration of no more than about 4 mm is typically required.

During introduction and withdrawal of the composite catheter system within the uterus, the distal ends of the respective microcatheters are withdrawn within the confines of the composite catheter to: 1) minimize the potential for trauma to the fertilized embryos contained therein, and 2) minimize the potential for trauma to the female reproductive organs during passage of the composite system therethrough. Alternatively to multiple microcatheters, a single catheter or a larger conventional catheter could be used.

The invention includes insertion, under direct observation, of embryos within the uterine endometrium of women undergoing in vitro fertilization. This site of embryo deposition more closely approximates the normal course of events than does conventional IVF. Conventional blind transfer techniques result in the deposition of in vitro fertilized embryos on the outer surface of the endometrium of the uterus. Subendometrial deposition of fertilized embryos could afford a higher pregnancy rate relative to conventional techniques.

Individuals subjected to the invention can expect several benefits. Pregnancy rates and efficiency of therapy are likely to improve. Tile ectopic pregnancy rate, which is currently approximately 5% for IVF pregnancies, would decrease since inserted embryos are unlikely to migrate into the fallopian tube from their endometrial implantation site.

Pregnancy rates per cycle are likely to be higher, with lower cost of therapy. Better efficiency of embryo transfer would require fewer embryos per attempt and therefore a lower risk of multiple pregnancies with less need for aggressive ovarian stimulation protocols. By utilizing embryo freezing, an oocyte retrieval would result in a greater number of embryo transfers and higher pregnancy rate per retrieval. Improving in vitro fertilization pregnancy rates would ultimately result in fewer invasive surgical therapies for infertility, such as laparoscopy and laparotomy, resulting in a significant reduction of the cost of therapy along with improved safety.

For best results, the invention can be practiced as follows. Patients requiring in vitro fertilization undergo a standard ovarian stimulation protocol. The protocol includes using conventional gonadotropin releasing hormone agonist pituitary suppression and gonadotropin ovarian stimulation discussed below. Subsequently, the patients undergo transvaginal ultrasound guided oocyte retrieval and in vitro fertilization by conventional methods well known to those of skill in the art. For example, see Meldrum, et al., "Evolution of a highly successful in vitro fertilization-embryo transfer program," Fertility & Sterility, 48(1):86 (July, 1987).

Embryo transfer is performed by hysteroscopically guided endometrial insertion of embryos according to the invention and more fully discussed below. Patients are monitored for response to ovarian stimulation, endometrial development, oocytes retrieved, fertilization and cleavage rates, numbers of embryos transferred, and pregnancy rates.

Estrogen levels by radioimmunoassay, follicle number and diameter, and endometrial development by ultrasound are monitored as is known in the art. The number and quality of oocytes retrieved, semen motility and count, oocyte fertilization, embryo cleavage rates, and embryo quality are observed microscopically. Measures of pregnancy outcome include human chorionic gonadotropin (hCG) levels at days 12 and 14 following transfer, ultrasonic evidence of gestational sacs, and ultimate pregnancy outcomes. Safety parameters are well known and include the presence or absence of uterine cramps, rated by the patient, and the ease of transfer and presence or absence of cervical bleeding, rated by the physician.

As is conventional, selected patients are preferably under the age of 40 with unexplained infertility, tubal factor infertility, or mild male factor infertility (total motile sperm concentration of >10 million per ml). Patients are screened for cervical infection by a cervical swab culture for aerobic organisms, gonorrhea, chlamydia, ureaplasma and mycoplasma. Patients with clinical or cultural evidence of cervical infection are treated and cure is verified by repeat culture and examination. Endometrial thickness on an unstimulated ovulation cycle should be at least 9 mm and less than 13 mm. Patients with known abnormalities of the implantation site, i.e. poor endometrial development, large myomas, or polyps should be excluded. Preferably patients have a cycle day 2 or 3 follicle stimulating hormone (FSH) level less than 16, and are undergoing a gonadotropin releasing hormone (GnRH) agonist down-regulated, gonadotropin stimulated ovarian stimulation in preparation for in vitro fertilization as discussed below.

Patients undergo a cycle of in vitro fertilization hormonal therapy according to standard protocols known to one of ordinary skill in the art. See Meldrum (July, 1987). Therapy includes pituitary down-regulation with a GnRH agonist (LUPRO ™, TAP Pharmaceuticals, North Chicago, Ill. or SYNAREL ™, Syntex, Palo Alto, Calif.), followed by ovarian stimulation with the gonadotropins human menopausal gonadotropin (hMG) and human FSH (hFSH) (PERGONAL ™ and METRODIN ™, respectively, SERONO Laboratories, Randoff, Mass.). Serum estradiol levels are monitored. Follicular diameter and endometrial maturation are determined ultrasonographically. At the onset of menses, an initial serum estradiol and vaginal ultrasonography confirm down-regulation of the pituitary and the absence of ovarian cysts.

By convention, stimulation day 1 is defined as the date of initiation of gonadotropin therapy. Gonadotropins are administered by the patient or partner by injection once or twice a day. An ultrasonogram and serum estradiol measurement are performed on stimulation day 8 and then periodically monitored until follicle maturity, defined as two follicles monitored until follicle maturity, defined as two follicles greater than or equal to 18 mm diameter and a serum estradiol greater than 550 picograms per milliliter (pg/ml). Patients with a peak estradiol of over 5000 pg/ml are preferably excluded. At follicle maturity, patients receive 10,000 units of hCG and undergo transvaginal ultrasonography guided oocyte retrieval about 36 hours later as conventionally practiced by those of skill in the art.

Embryos are cultured according to standard protocol under oil in individual droplets of media. For example, see Cohen, et al., *Micromanipulation of Human Gametes and Embryos*, 142–144, Raven Press, NY (1992). Conditions for embryo culture include a pH and temperature controlled environment according to established protocol. For example, see Keel, B. A. and B. W. Webster, *CRC Handbook of the Laboratory Diagnosis & Treatment of Infertility*, CRC Press (1990) and Cohen, et al., (1992).

At embryo transfer, 48 hours following oocyte aspiration, patients receive six embryos in transfer by the inventive technique of hysteroscopically guided endometrial insertion of embryos. Embryos are loaded according to the invention into individual microcatheters (such as those available from Danforth Biomedical, Inc., Menlo Park, Calif.) by placing the microcatheter(s) in a catheter sleeve and attaching a syringe, preferably a microliter syringe, to the external Luer lock end of the microcatheter. Preferably, the sleeve accommodates three microcatheters, but a sleeve having a single port or any number of ports dimensioned to accept a microcatheter could be used. The tip of each microcatheter is advanced from the sleeve and the microcatheter is rinsed twice with a physiologic irrigant, for example, stock Ham's F-10, a standard tissue culture medium (available from GIBCO, New York).

The microcatheters of the invention and the syringe are loaded with medium followed by a small air bubble to separate the embryos and medium. Embryos are loaded by aspirating them in a 5–10 microliter volume with the microliter syringe, preferably drawing two embryos into each microcatheter. The microcatheter tip is retracted into the sleeve.

Embryo loading occurs at a temperature of 37° Celsius (C) under an oil bath in a sterile environment according to established protocols. For example, see Veeck, et al., "Atlas of the Human Oocyte & Early Conceptus," Vol. III, Williams & Wilkins (1986). Embryo loading only occurs after identification of an appropriate transfer location. Embryos are away from a warmer for no more than two minutes. If transfer is not accomplished in that time, embryos are returned to the laboratory for a ten minute re-equilibration period.

The physician irrigates the vagina at least once with a sterile solution. Preferably irrigation includes three washes of sterile saline followed by a single irrigation of sterile media. According to the invention, hysteroscopy is initiated using a flexible 30 centimeter (cm) 2.1 mm diameter hysteroscope (available from Intramed, San Diego) and $CO_2$ gas insufflation. The endometrial transfer location is evaluated for its position in the uterine cavity. Preferred locations according to the invention are in the midline and 1 cm below the superior limit of the fundus in the posterior wall. The presence of normal lush mid-cycle endometrium, and the absence of polyps, myomas, endometrial tags, bleeding and vascular anomalies are preferred. When a transfer location is identified within the uterus, gas is evacuated and the catheter sleeve containing the transfer microcatheters is inserted through the operating channel of the hysteroscope into the endometrial cavity.

The tip of a microcatheter is advanced from the sleeve and inserted into the endometrial lining according to the invention to a depth of about 1.0 mm. Depth can be measured by marks at 3, 5, and 10 mm from the tip of the microcatheter. The embryo is injected by ejecting a 5–10 microliter volume from the syringe. The microcatheter is pulled back into the sleeve.

If multiple microcatheters are used as is preferred, the tip of the hysteroscope is moved 0.5 to 1 cm laterally and the second microcatheter is advanced. The remaining embryos are injected similarly to the first. The catheter sleeve containing the transfer microcatheters is removed and the microcatheters are inspected in the laboratory to determine if all of the embryos were injected. If less than 50% of the embryos were successfully inserted, a second attempt at transfer is performed. The practitioner rates the ease of transfer and the presence or absence of bleeding and cramping.

Patients are observed at bedrest for two hours following transfer according to standard in vitro fertilization protocols. For example, see Veeck, et al., (1986). The patient rates the presence or absence of cramps or discomfort relative to her normal menstrual periods. The partner observes the patient at home for 18 hours, noting information about bleeding, cramps, lightheadedness, or nausea. The cervix is examined by vaginal speculum at 2 and 5 days after transfer for evidence of bleeding or infection.

As in conventional protocols, intramuscular progesterone supplementation is given from the day of oocyte retrieval up to luteal phase day 14, and serum pregnancy tests are measured on luteal phase days 12 and 14. In the event of a positive pregnancy test, the patient is maintained on hCG 5000 units every Monday, Wednesday, and Friday until 10 weeks gestation. Vaginal ultrasound is performed at gestational ages of 7 and 10 weeks to determine presence of a gestational sac, fetal pole, yolk sac, and heart beat, and to monitor the growth of the fetus.

One skilled in the art is aware that hysteroscopy may cause some cramping and cervical or uterine bleeding. Insertion of the hysteroscope could result in a uterine or tubal infection, formation of a false passage within the cervix or perforation of the uterus. Bleeding within the uterine cavity could disturb embryo implantation. Embryo transfer could fail because the hysteroscope could not be inserted into the uterus, or the transfer catheter could not be inserted into the endometrium. Embryos occasionally stick to plastic surfaces, and may not eject from the catheter when inserted. Pregnancy might not occur because of failure of the technique or abnormal embryos.

The risks mentioned above attend IVF techniques generally and are not unique to the invention. Measures to minimize these risks when practicing the invention include use of a small diameter 2.1 mm hysteroscope, and visualizing the endocervical canal and endometrial cavity during insertion. Bacterial contamination is reduced by use of pretreatment cervical cultures, and vaginal irrigation with sterile saline and transfer medium prior to transfer. $CO_2$ insufflation improves visualization. The hysteroscope is steerable, allowing it to negotiate the cervical curvature.

The foregoing is offered primarily for purposes of illustration. It will be readily apparent to those skilled in the art that the operating conditions, materials, procedural steps and other parameters of the system described herein may be further modified or substituted in various ways without departing from the spirit and scope of the invention. For example, although preferred embodiments have been described for humans, the invention can find veterinary use. Mammals including livestock could be the recipients of the inventive technique. Also, use of more than one microcatheter contained in a sleeve for each IVF attempt is preferred, but the practitioner could use a single conventional catheter with or without a sleeve. Thus the invention is not limited by the preceding description, but rather by the appended claims.

What is claimed is:

1. A method for implantation of an embryo into a mammal comprising:
   (a) placing at least one embryo in a catheter having an elongate tubular body and a distal tip;
   (b) introducing the distal tip through the mammal's cervical os into the mammal's endometrial cavity;
   (c) directing the distal tip into the mammal's uterine tissue; and
   (d) depositing the embryo into the uterine tissue beneath the endometrial surface.

2. The method of claim 1 wherein the mammal is a human.

3. The method of claim 1 wherein step (a) further comprises placing said at least one embryo in contact with a nonstick surface located at the distal tip of the catheter.

4. The method of claim 1 wherein step (a) further comprises placing said at least one embryo in contact with a surface comprised of polytetrafluoroethylene located at the distal tip of the catheter.

5. The method of claim 1 further comprising performing at least one of steps (b), (c), and (d) using fiberoptic guidance.

6. The method of claim 1 wherein step (d) comprises depositing the embryo at a depth of from about 0.5 mm to about 5 mm beneath the endometrial surface.

7. The method of claim 6 wherein step (d) comprises depositing the embryo at a depth of from about 0.5 mm to about 2 mm beneath the endometrial surface.

8. The method of claim 7 wherein step (d) comprises depositing the embryo at a depth of about 1.0 mm beneath the endometrial surface.

9. The method of claim 1 wherein step (d) is performed by flushing the catheter with a physiologic irrigant to assist with depositing the embryo.

10. The method of claim 9 wherein the physiologic irrigant is a member selected from the group consisting of amniotic fluid, follicular fluid, a saline solution, a Ringer's solution, and a culture medium.

11. The method of claim 10 wherein the culture medium is stock Ham's F-10.

12. A method for implantation of an embryo into a human comprising:
   (a) placing at least one embryo in a distal tip of a microcatheter having an elongate tubular body, the distal tip including a nonstick surface;
   (b) introducing the distal tip through the human's cervical os into the human's endometrial cavity;
   (c) directing the distal tip into the human's uterine tissue at a depth of about 0.5 mm to about 4 mm; and
   (d) flushing the microcatheter with a physiologic irrigant, thereby depositing the embryo into the uterine tissue at a depth of about 0.5 mm to about 4 mm beneath the endometrial surface.

13. The method of claim 12 further comprising the step of inserting one to five of the microcatheters within a sleeve, thereby assisting with step (b).

14. The method of claim 13 further comprising the step of inserting three microcatheters within the sleeve, thereby assisting with step (b).

15. The method of claim 13 further comprising the step of selecting a sleeve having a diameter of about 0.5 to 2 mm, thereby assisting with step (b).

16. The method of claim 13 further comprising the step of selecting a sleeve having a curved dimension, thereby assisting with step (b).

17. The method of claim 12 wherein fiberoptic guidance is used to assist in the performance of at least one of steps (b), (c), and (d).

18. The method of claim 17 wherein said fiberoptic guidance is provided by an endoscope of the type having a hollow tubular channel, said channel adapted for receipt of the catheter and dimensioned to permit protrusion of the distal tip of the catheter from the distal end of the channel.

19. The method of claim 12 further comprising the step of selecting a microcatheter wherein the distal tip of the microcatheter has a diameter narrower than a diameter of the elongate body, thereby assisting with step (b).

20. The method of claim 12 further comprising the step of selecting a microcatheter wherein the distal tip of the microcatheter has a diameter of from about 0.1 mm to about 1.0 mm, thereby assisting with step (b).

21. The method of claim 12, further comprising the step of selecting a microcatheter wherein the distal tip of the microcatheter is sufficiently sharp for inserting the distal tip beneath the endometrial surface, thereby assisting with step (c).

22. The method of claim 12 wherein the physiologic irrigant is a culture medium.

23. The method of claim 22 wherein the culture medium is stock Ham's F-10.

* * * * *